United States Patent
Baggett et al.

(10) Patent No.: US 10,041,789 B2
(45) Date of Patent: Aug. 7, 2018

(54) INTEGRATED EMISSIVITY SENSOR ALIGNMENT CHARACTERIZATION

(71) Applicant: Axcelis Technologies, Inc., Beverly, MA (US)

(72) Inventors: John F. Baggett, Amesbury, MA (US); Joseph Ferrara, Georgetown, MA (US)

(73) Assignee: Axcelis Technologies, Inc., Beverly, MA (US)

( * ) Notice: Subject to any disclaimer, the term of this patent is extended or adjusted under 35 U.S.C. 154(b) by 0 days.

(21) Appl. No.: 15/281,757

(22) Filed: Sep. 30, 2016

(65) Prior Publication Data
US 2018/0094921 A1   Apr. 5, 2018

(51) Int. Cl.
| | |
|---|---|
| *G01B 11/27* | (2006.01) |
| *G01N 21/59* | (2006.01) |
| *G01N 21/84* | (2006.01) |
| *H01L 21/68* | (2006.01) |

(52) U.S. Cl.
CPC ........... *G01B 11/272* (2013.01); *G01N 21/59* (2013.01); *G01N 21/84* (2013.01); *H01L 21/681* (2013.01); *G01N 2021/8416* (2013.01)

(58) Field of Classification Search
None
See application file for complete search history.

(56) References Cited

U.S. PATENT DOCUMENTS

| | | | | |
|---|---|---|---|---|
| 5,153,419 A | * | 10/1992 | Takahashi | G03F 7/70141 250/201.1 |
| 5,452,078 A | * | 9/1995 | Cheng | G01B 11/272 250/548 |
| 5,644,400 A | * | 7/1997 | Mundt | G01B 11/08 356/150 |
| 5,740,034 A | * | 4/1998 | Saeki | H01L 21/681 356/601 |
| 6,162,008 A | * | 12/2000 | Perkins | G01B 11/24 198/394 |
| 6,222,991 B1 | | 4/2001 | Davenport | |

(Continued)

FOREIGN PATENT DOCUMENTS

WO   2014/074861 A1   5/2014

OTHER PUBLICATIONS

International Search Report and Written Opinion dated Dec. 11, 2017 for International Application PCT/US2017/052139.

*Primary Examiner* — Shawn Decenzo
(74) *Attorney, Agent, or Firm* — Eschweiler & Potashnik, LLC (57) ABSTRACT

A workpiece alignment system has a workpiece support to support a workpiece. A first light emitter directs a first light beam toward the workpiece. A first light receiver receives the first light beam. A rotation device rotates the workpiece support about a support axis. A second light emitter directs a second light beam toward a peripheral region of the workpiece. A second light receiver receives the second light beam concurrent with the rotation of the workpiece. A controller determines a transmissivity of the workpiece based on a total initial emittance of the first light beam a transmission of the first light beam through the workpiece. The controller determines a position of the workpiece with respect to the support axis based, at least in part, on a rotational position of the workpiece, a portion of the second light beam received, and the determined transmissivity.

20 Claims, 4 Drawing Sheets

(56) References Cited

U.S. PATENT DOCUMENTS

| | | | | |
|---|---|---|---|---|
| 6,489,626 | B2* | 12/2002 | van der Muehlen | H01L 21/681 250/559.29 |
| 7,042,568 | B2* | 5/2006 | Mayo | H01L 21/681 250/559.29 |
| 7,379,174 | B2 | 5/2008 | Miyajima et al. | |
| 7,737,426 | B2* | 6/2010 | Takahashi | H01L 21/681 250/559.36 |
| 7,973,300 | B2* | 7/2011 | Takahashi | H01L 21/681 250/559.36 |
| 2015/0009498 | A1* | 1/2015 | Zell | G01B 11/27 356/399 |
| 2015/0176980 | A1* | 6/2015 | Jensen | H01L 21/681 356/614 |
| 2017/0050211 | A1* | 2/2017 | Inagaki | B05B 9/03 |

* cited by examiner

INTEGRATED EMISSIVITY SENSOR ALIGNMENT CHARACTERIZATION

FIELD

The present disclosure relates generally to workpiece processing systems and methods for processing workpieces, and more specifically to a system and method for handling and aligning workpieces having varying light transmission properties.

BACKGROUND

In semiconductor processing, many operations may be performed on a single workpiece or semiconductor wafer. In general, each processing operation on a workpiece is typically performed in a particular order, wherein each operation waits until completion of a preceding operation. In many processing operations, a particular orientation of the workpiece and/or knowledge of the position of the workpiece with respect to a workpiece holder is needed in order to properly process or handle the workpiece. For example, operations such as an exchange of workpieces between transport carriers or storage cassettes and the processing system and a transfer of the workpieces from an atmospheric environment into an evacuated environment of a process chamber of the processing system through one or more load lock chambers may require specific orientation(s) or knowledge of the spatial position of the workpiece for proper workpiece handling and processing.

An orientation of the workpiece (e.g., notch alignment) may be performed within the evacuated environment or atmospheric environment via a light presence sensor, whereby a beam of light is emitted by a light emitter and directed toward the workpiece concurrent to a rotation of the workpiece with respect to the beam of light. A variation in light received by a light receiver can be then used to determine the position of notch defined in the workpiece and/or an eccentricity of a position of the workpiece, depending on how the light is fully or partially received. One such system is disclosed in U.S. Pat. No. 5,740,034 to Hiroaki Saeki, whereby a waveform associated with the received light signals is utilized to determine the position of the notch and/or eccentric position of the workpiece.

Conventionally, such positioning via light presence sensors has been adequate for accurately determining the position of a workpiece that is opaque to the light emitted, such seen in conventional silicon substrates. However, when substrates or workpieces undergoing processing in the same processing system differ materially from one another (e.g., silicon versus silicon carbide), the use of a conventional light presence sensor and aligner can lead to various errors in positioning, specifically when the substrate is partially transparent to the light emitted. For example, a difference in transmission from one substrate to another can lead a significant error in positioning using conventional alignment systems and methods. The transmissivity and emissivity from workpiece to workpiece can vary with the constituency, thickness and coatings disposed on the particular workpiece. As such, when changing from one workpiece type to another (or one coating to another), conventional alignment systems fail to provide adequate positioning data without significant changes to the alignment systems, themselves, such as changing the wavelength of light emitted therefrom.

SUMMARY

The present disclosure advantageously overcomes the limitations of the prior art by providing a system, apparatus, and method for accurately determining a position of workpieces having various emissivities and/or transmissivities, thereby minimizing costs of ownership associated with the systems. More particularly, the present disclosure provides a system and method for advantageously determining a transmissivity of the workpiece and utilizing the transmissivity as an input to an alignment apparatus, whereby signals associated with the alignment apparatus are adjusted based on the transmissivity. The present disclosure thus provides a positioning solution for practically any substrate material and thickness, regardless of various coatings or properties of the substrate.

Accordingly, the following presents a simplified summary of the disclosure in order to provide a basic understanding of some aspects of the disclosure. This summary is not an extensive overview of the disclosure. It is intended to neither identify key or critical elements of the disclosure nor delineate the scope of the disclosure. Its purpose is to present some concepts of the disclosure in a simplified form as a prelude to the more detailed description that is presented later.

The present disclosure is directed generally toward a workpiece handling system and method for handling workpieces. In particular, a workpiece alignment system and method for using same are provided. In accordance with one exemplary aspect of the disclosure, workpiece alignment system comprises a workpiece support configured to selectively support a workpiece along a workpiece plane. A first light emission apparatus is positioned on a first side of the workpiece plane, wherein the first light emission apparatus is configured to direct a first beam of light along a first path toward the workpiece plane. In one example, the first path is associated with a central region of the workpiece, wherein the central region of the workpiece intercepts an entirety of the first beam of light directed toward the surface of the workpiece. In another example, the first light emission apparatus is positioned anywhere such that the first path is physically obstructed in its entirety by the workpiece.

A first light receiver apparatus, for example, is further positioned on a second side of the workpiece plane and along the first path, wherein the second side is opposite the first side. The first light receiver apparatus, for example, is configured to receive the first beam of light. A rotation device is further operably coupled to the workpiece support, wherein the rotation device is configured to selectively rotate the workpiece support about a support axis. The support axis, for example, is perpendicular to the workpiece plane.

In accordance with one aspect, a second light emission apparatus is positioned on one of the first side and second side of the workpiece plane, wherein the second light emission apparatus is configured to direct a second beam of light along a second path. The second path, for example, is associated with a peripheral region of the workpiece. In one particular example, the first emission apparatus and second emission apparatus are configured to emit an equivalent wavelength of light. The equivalent wavelength of light emitted by the first emission apparatus and second emission apparatus, for example, may be determined based on the constituency of the workpiece. A second light receiver apparatus is further provided and configured to receive the second beam of light concurrent with the rotation of the workpiece support.

In accordance with the present disclosure, the workpiece alignment system further comprises a controller, wherein in one exemplary aspect, the controller is configured to determine a transmissivity of the workpiece based on a total initial emittance of the first beam of light and a transmitted amount of the first beam of light that is received through the workpiece by the first receiver apparatus. For example, the transmitted amount of the first beam of light is based, at least in part on one or more of a material constituency of the workpiece, one or more layers formed on the workpiece, and one or more operations previously performed on the workpiece, such as a previous ion implantation or other semiconductor process previously performed on the workpiece.

The controller of the present disclosure is further configured to determine a position of the workpiece with respect to the support axis based, at least in part, on a rotational position of the workpiece support, at least a portion of the second beam of light that is received by the second receiver, and the determined transmissivity of the workpiece. The at least a portion of the second beam of light that is received by the second receiver, for example, is associated with the rotational position of the workpiece support. In one example, the position of the workpiece that is determined by the controller comprises a two-dimensional offset of a center of the workpiece from the support axis along the workpiece plane. The position of the workpiece may further comprise a rotational position of the workpiece about the support axis, wherein the rotational position of the workpiece about the support axis is associated with an edge feature of the workpiece, and wherein the controller is further configured to determine the position of the workpiece with respect to the support axis based on the edge feature of the workpiece. The edge feature, for example, may comprise a notch, flat, or other feature associated with a periphery of the workpiece.

In accordance with another exemplary aspect, the controller is configured to determine a first waveform, wherein the first waveform is defined by the at least a portion of the second beam of light received by the second receiver at a plurality of rotational positions of the workpiece support. The controller, for example, is further configured to determine the position of the workpiece with respect to the support axis based on the first waveform. In one example, the controller is further configured to proportion the first waveform based on the transmissivity of the workpiece. For example, the controller is configured to scale the at least a portion of the second beam of light received by the second receiver at the plurality of rotational positions of the workpiece support based on the transmissivity of the workpiece, therein normalizing the first waveform. In another example, the transmitted amount of the first beam of light is defined as a percentage of a total initial emittance of the first beam of light.

In accordance with another example, the first light emission apparatus and second light emission apparatus comprise separate light emission apparatuses, wherein the first light receiver apparatus and second light receiver apparatus likewise comprise separate light received apparatuses. In another example, a single light emission apparatus comprises the first light emission apparatus and second light emission apparatus, and wherein a single light received apparatus comprises the first light receiver apparatus and second light receiver apparatus, wherein the first path and second path are collinear.

In accordance with another exemplary aspect, a method is provided for aligning a workpiece. The method comprises placing a workpiece on a workpiece support and directing a first beam of light toward a first side of the workpiece along a first path. In one example, an entirety of the first beam of light is physically intercepted by the workpiece. Any portion of the first beam of light that is transmitted through the workpiece to a second side of the workpiece is received and a transmissivity of the workpiece based on the first beam of light that is transmitted through the workpiece.

A second beam of light is further directed toward a periphery of the workpiece along a second path, and the workpiece is rotated about a support axis. The first beam of light and second beam of light, for example, have equivalent wavelengths. The second beam of light is further received concurrent with the rotation of the workpiece, whereby a position of the workpiece with respect to the support axis is determined based, at least in part, on a rotational position of the workpiece about the support axis and the second beam of light that is received, wherein the second beam of light is proportioned according to the determined transmissivity of the workpiece. The second beam of light, for example, is at least partially obscured by the periphery of the workpiece concurrent with the rotation of the workpiece.

Directing the first beam of light toward the first side of the workpiece, for example, comprises directing the first beam of light toward a central region of the workpiece. In another example, determining the position of the workpiece with respect to the support axis comprises determining one or more of a rotational position of the workpiece about the support axis and a two-dimensional offset of a center of the workpiece from the support axis.

To the accomplishment of the foregoing and related ends, the disclosure comprises the features hereinafter fully described and particularly pointed out in the claims. The following description and the annexed drawings set forth in detail certain illustrative embodiments of the disclosure. These embodiments are indicative, however, of a few of the various ways in which the principles of the disclosure may be employed. Other objects, advantages and novel features of the disclosure will become apparent from the following detailed description of the disclosure when considered in conjunction with the drawings.

DETAILED DESCRIPTION

The present disclosure is directed generally toward a workpiece handling system for semiconductor processes, and more particularly, to an alignment apparatus configured to characterize and align workpieces having varying light transmission properties. Accordingly, the present disclosure will now be described with reference to the drawings, wherein like reference numerals may be used to refer to like elements throughout. It should be understood that the description of these aspects are merely illustrative and that they should not be interpreted in a limiting sense. In the following description, for purposes of explanation, numerous specific details are set forth in order to provide a thorough understanding of the present disclosure. It will be evident to one skilled in the art, however, that the present disclosure may be practiced without these specific details.

A conventional aligner comprises a light emitter and a light receiver, whereby the light emitter directs a beam of light toward an edge of a workpiece, whereby the aligner further determines an amount of the emitted light that is blocked from reaching the light receiver as the workpiece is rotated about a rotation axis. For example, if a center of the workpiece is offset from the rotation axis of the aligner, variations will be present in the amount of light received by the light receiver as the workpiece blocks varying amounts of the emitted light as the workpiece is rotated. The amount of blocked light, for example, is represented as a percentage of the total light that is emitted. The amount and variation of light received is subsequently converted to a dimension associated with the workpiece (e.g., an offset), whereby, in one example, the dimension is utilized by an end-effector to retrieve the workpiece at the center of the workpiece.

One exemplary conversion of the percentage of blocked light to the offset dimension utilizes a fixture to characterize the system, whereby a curve is defined depicting the position of the workpiece. The fixture, for example, simulates a workpiece that is offset in multiple positions, thus correlating the percentage of light that is blocked at each of such multiple positions. For example, if 50% of the emitted light is received by the light receiver, a change in the amount of light received by the light receiver can be used to determine a position of the workpiece, based on the rotational position of the workpiece and how much light is blocked from the light receiver by the workpiece. Accordingly, a determination can be made to reflect whether the workpiece is centered, or a location of key features such as a notch or flat defined in the workpiece, based on this information.

To simulate a conventional silicon (Si) wafer, a fixture is provided that is opaque to the light emitted by the aligner, as a conventional silicon wafer is also opaque to the light emitted by the aligner. A silicon carbide (SiC) wafer, however, is partially transparent to such light emitted by the aligner. Thus, in the same position on the aligner, a silicon wafer and a silicon carbide wafer will result in two different amounts of light received.

Therefore, if silicon carbide wafers are to be processed, a fixture that simulates a silicon carbide workpiece is also provided to correlate the percentage of the light that is blocked at each of such multiple positions. Furthermore, a thickness silicon carbide wafer can also vary the amount of light transmitted through the silicon carbide wafer. Additionally, various coatings on the silicon carbide wafer can result in yet other variations in light transmission. As such, a myriad of fixtures simulating all such variations in material composition, thickness, and coating(s) would be necessary to characterize all such workpieces. Providing such a myriad of fixtures would unsatisfactorily affect cost and productivity, and would likely incur ongoing changes to the alignment system in order to accommodate any changes in coatings, thickness, etc. of the workpieces.

Alternatively, the light source can be modified to provide a wavelength of light that does not transmit through the desired workpiece. However, again, such modifications of light sources are time consuming, costly, and may not account for other variations in the workpiece, such as any layers formed thereon, various thicknesses of coatings, reflectance from the surface of the workpiece, and so on. Further, since any such variations can have a potential effect on the sensing of the light, calibration of the alignment system are not as simple as calibrating the aligner to particular material.

The present disclosure advantageously provides an alignment system configured to measure a transmissivity of a workpiece in-situ, whereby the transmissivity measurement is further utilized as a parameter in an alignment algorithm. The present disclosure provides a sensor (e.g., an emissivity or transmissivity sensor) for sensing transmission prior to, or concurrent with, the workpiece being positioned on the aligner, whereby a determination is made regarding how much of an amount of light transmitted from a light source is transmitted through the workpiece. As such, transmission, reflection, and emissivity information is attained and fed back to the alignment system so that the workpiece, comprised of any material or having any coatings or operations performed thereon, can be accurately aligned.

Figure 1:
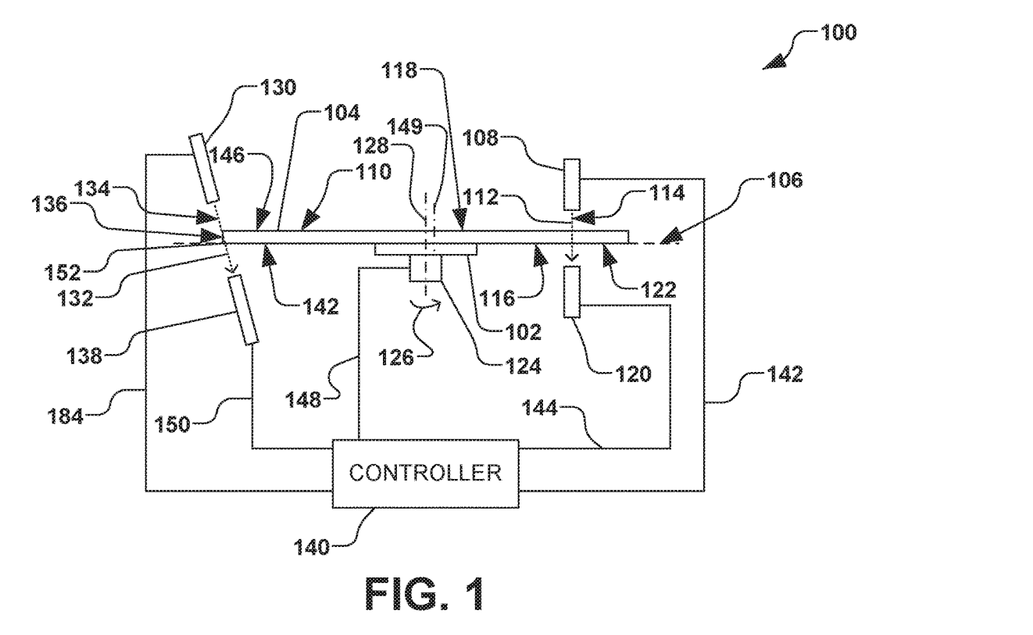
FIG. 1 illustrates a block diagram of an exemplary workpiece alignment system in accordance with one aspect of the present disclosure.

Referring now to the figures, FIG. 1 illustrates an exemplary workpiece alignment system 100 in accordance with one or more aspects of the present disclosure. The workpiece alignment system 100, for example, comprises a workpiece support 102 configured to selectively support a workpiece 104 along a workpiece plane 106. The workpiece support 102, for example, may comprise any number of support mechanisms, such as pins, plates, or other mechanisms (not shown) operable to selectively support the workpiece 104.

In accordance with one example, a first light emission apparatus 108 is positioned on a first side 110 of the workpiece plane 106, wherein the first light emission apparatus is configured to direct a first beam of light 112 along a first path 114 toward the workpiece plane. In one example, the first path 114 is associated with a central region 116 of the workpiece 104, wherein the central region of the workpiece intercepts an entirety of the first beam of light 112 directed toward a surface 118 of the workpiece. In another example, the first light emission apparatus 108 is positioned anywhere such that the first path 114 is physically obstructed in its entirety by the workpiece 104.

A first light receiver apparatus 120, for example, is further positioned on a second side 122 of the workpiece plane 106 and along the first path 112, wherein the second side is opposite the first side 110 of the workpiece plane. The first light receiver apparatus 120, for example, is configured to receive the first beam of light 112. A rotation device 124 is further operably coupled to the workpiece support 102, wherein the rotation device is configured to selectively rotate (e.g., illustrated by arrow 126) the workpiece support about a support axis 128. The support axis 128, for example, is perpendicular to the workpiece plane 106.

The first light emission apparatus 108 and first light receiver apparatus 120 of FIG. 1 are illustrated as being proximate to the workpiece support 102 of the workpiece alignment system 100, whereby the first path 114 is associated with the central region 116 of the workpiece 104 when the workpiece is supported by the workpiece support. However, it should be noted that the first light emission apparatus 108 and first light receiver apparatus 120 may be located at any location where the workpiece 104 is supported prior to the workpiece being placed on the workpiece support 102.

Figure 7:
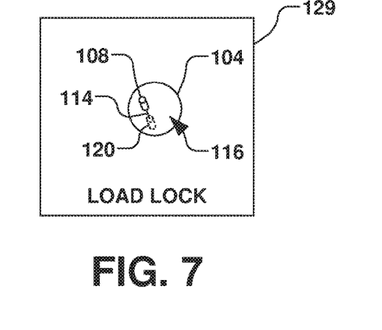
FIG. 7 illustrates a block diagram of a first path of a first beam of light passing through a workpiece in accordance with an example of the present disclosure.

For example, the first light emission apparatus 108 and first light receiver apparatus 120 may be positioned within a load lock chamber 129 illustrated in FIG. 7 or at any other location upstream of the rotation device 124 of FIG. 1. As such, the workpiece 104 may be supported on a secondary workpiece support (not shown), whereby the first path 114 is likewise associated with the central region 116 of the workpiece. Thus, the workpiece support 102 of FIG. 1 may be considered as a single structure configured to support the workpiece 104 in a single location, or multiple, independent structures configured to support the workpiece at multiple locations.

In accordance with one exemplary aspect, a second light emission apparatus 130 is further positioned on one of the first side 110 and second side 122 of the workpiece plane 106, wherein the second light emission apparatus is configured to direct a second beam of light 132 along a second path 134. The second path 134, for example, is associated with a peripheral region 136 of the workpiece 104. In one particular example, the first emission apparatus 108 and second emission apparatus 130 are configured to emit an equivalent wavelength of light. The equivalent wavelength of light emitted by the first emission apparatus 108 and second emission apparatus 130, for example, may be determined based on the constituency of the workpiece 104. A second light receiver apparatus 138 is further provided and configured to receive the second beam of light 132 concurrent with the rotation of the workpiece support 102 about the support axis 128.

In accordance with several aspects of the present disclosure, the workpiece alignment system 100 further comprises a controller 140, wherein the controller is configured to determine a transmissivity of the workpiece 104 based on a total initial emittance (indicated as a first emittance 142) of the first beam of light 112 and a first transmission 144 (e.g., transmitted amount) of the first beam of light that is received through the workpiece by the first receiver apparatus 120. For example, the first transmission 144 of the first beam of light 112 is based, at least in part on one or more of a material constituency of the workpiece 104, one or more layers (not shown) formed on the workpiece, and one or more operations previously performed on the workpiece, such as a previous ion implantation or other semiconductor process previously performed on the workpiece.

According to another example, the controller 140 is further configured to determine a position 146 of the workpiece 104 with respect to the support axis 128. It should be noted that the controller 140, for example, may comprise multiple individual controllers (not shown) associated with various components of the processing system, or may be a single controller for the whole system, and all such controllers are contemplated as falling within the scope of the present disclosure.

Figure 2:
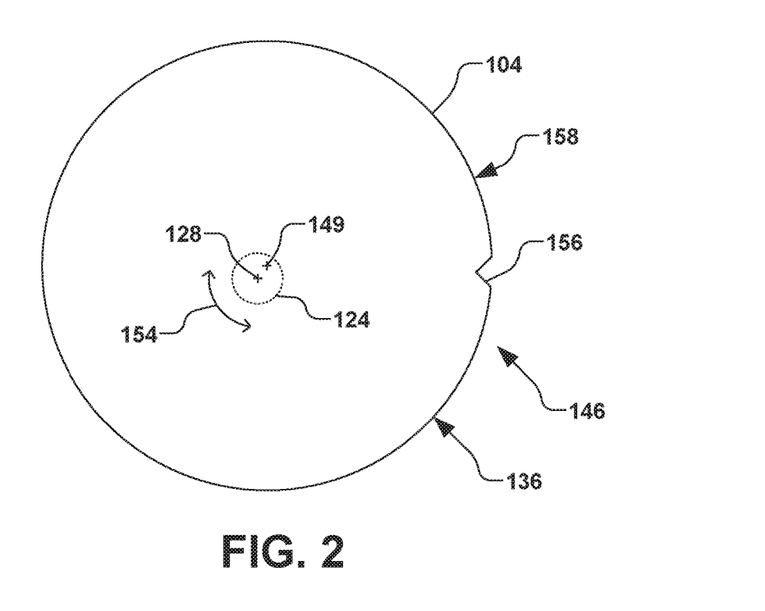
FIG. 2 is a plan view of an exemplary workpiece on a workpiece support of an exemplary alignment mechanism.

The position 146 of the workpiece 104, for example, may be determined by the controller 140, whereby the controller is configured to determine a center 149 of the workpiece 104 with respect to the rotational axis 128 of the workpiece support 124, as illustrated in FIG. 2. For example, as illustrated in FIG. 1, the determination of the position 146 of the workpiece 104 with respect to the support axis 128 is based, at least in part, on a rotational position 148 of the workpiece support 102, at least an output signal 150 indicative of a portion 152 of the second beam of light 132 that is received by the second receiver 138, and the determined transmissivity of the workpiece 104 (based on the first transmission 144).

The at least a portion 152 of the second beam of light 132 that is received by the second light receiver apparatus 138, for example, is associated with the rotational position 148 of the workpiece support 102. In one example, the position 146 of the workpiece 104 that is determined by the controller 140 comprises a two-dimensional offset of the center 149 of the workpiece from the support axis 128 along the workpiece plane 106, as illustrated in FIG. 2. The position 146 of the workpiece 104 may further comprise a rotational position 154 of the workpiece 104 about the support axis 128, wherein the rotational position of the workpiece about the support axis is associated with an edge feature 156 of the workpiece, and wherein the controller 140 of FIG. 1 is further configured to determine the position of the workpiece with respect to the support axis based on the edge feature of the workpiece. The edge feature 156 of FIG. 2, for example, may comprise a notch, flat, or other feature associated with a periphery 158 of the workpiece 104.

Figure 3:
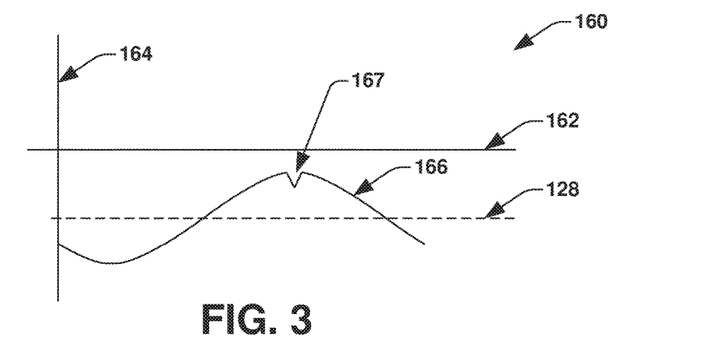
FIG. 3 is a plot of a sensed position of a workpiece versus a rotational position of the workpiece support according to another exemplary aspect of the disclosure.

FIG. 3, for example, illustrates a plot 160 of a rotational position 162 (e.g., provided by a servo motor or other apparatus associated with the rotation device 124 of FIG. 1) versus the output 164 from the light receiver apparatus 138 of FIG. 1, wherein the center 149 of the workpiece 104 can be extrapolated from an output signal curve 166 (from the output signal 150) indicating the passage of the edge feature 156 through the second beam of light 132 (e.g., illustrated in FIG. 3 at position 167) and a knowledge of the dimensions of the edge feature.

Figure 4:
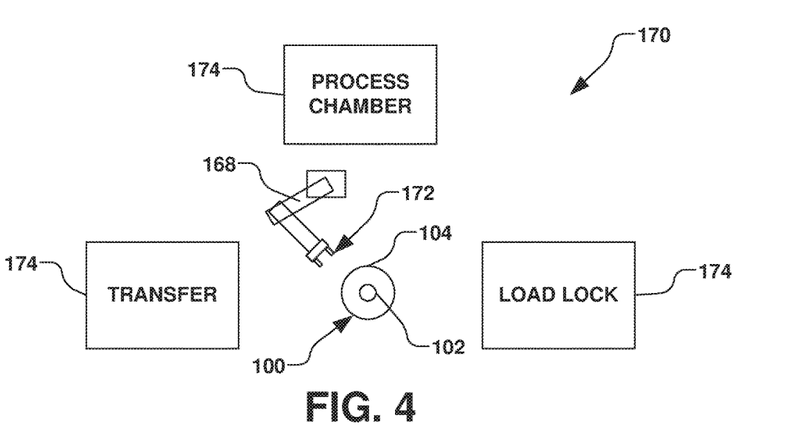
FIG. 4 illustrates the exemplary workpiece handling system incorporating the workpiece alignment system of FIG. 1.

Accordingly, the controller 140 of FIG. 1 can determine an offset vector value associated with the center 149 of the workpiece 104 which can be provided to a robot 168 illustrated in the workpiece handling system 170 of FIG. 4. The robot 168, for example, may be configured to pick the workpiece 104 from the workpiece support 102 based on the offset vector value, whereby the workpiece is generally centered with respect to a support member 172 when it is picked from workpiece alignment system 100 of FIG. 1. The rotational position of the workpiece 104 can be further utilized to rotationally align the workpiece with respect to the workpiece alignment system 100 prior to being picked by the robot 168 and transferred to one or more stations 174, such as a process chamber, load lock chamber, transfer system, or other apparatus utilized in processing of the workpiece.

Figure 5:
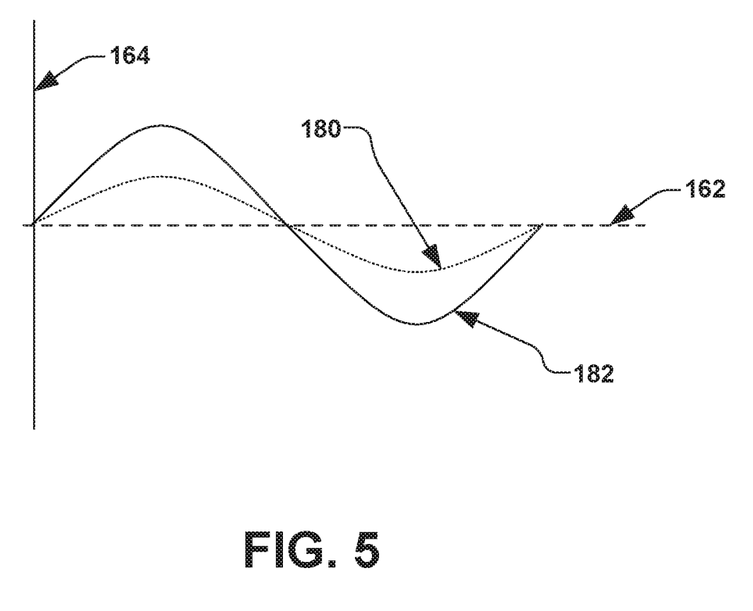
FIG. 5 a plot of a sensed position of workpiece and a normalized position of the workpiece versus a rotational position of the workpiece support according to another exemplary aspect of the disclosure.

In accordance with another exemplary aspect, the controller 140 of FIG. 1 is configured to determine a first waveform 180 illustrated in FIG. 5, wherein the first waveform is defined by the at least a portion of the second beam of light 132 received by the second receiver 138 at a plurality of rotational positions of the workpiece support 102. The controller 140 of FIG. 1, for example, is further thus configured to determine the position of the workpiece 104 with respect to the support axis 128 based on the first waveform 180 of FIG. 5. In one example, the controller 140 of FIG. 1 is further configured to proportion the first waveform 180 based on the determined transmissivity of the workpiece 104.

For example, the controller 140 is configured to scale the at least a portion 152 of the second beam of light 132 received by the second receiver 138 at the plurality of rotational positions of the workpiece support 102 based on the determined transmissivity of the workpiece, therein normalizing the first waveform 180 to a second waveform 182 of FIG. 5. In another example, the at least a portion 152 of the first beam of light 132 of FIG. 1 is defined as a percentage of a total initial emittance (e.g., the first transmission 144 of the first beam of light 112 of FIG. 1), whereby the first waveform 180 is proportionately converted to the second waveform 182 of FIG. 5.

Figure 8:
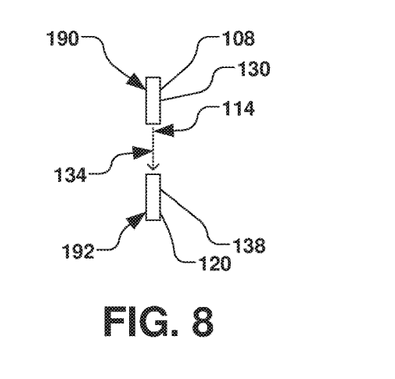
FIG. 8 illustrates a block diagram of a single light emission apparatus and single light receiver apparatus having collinear first and second paths in accordance with an example of the present disclosure.

In accordance with another example of the disclosure, the first light emission apparatus 108 and second light emission apparatus 130 comprise separate light emission apparatuses, wherein the first light receiver apparatus and second light receiver apparatus likewise comprise respective separate first and second light receiver apparatuses 120, 138. In another example, a single light emission apparatus 190 shown in FIG. 8 comprises the first light emission apparatus 108 and second light emission apparatus 130, and wherein a single light receiver apparatus 192 comprises the first light receiver apparatus 120 and second light receiver apparatus 138, wherein the first path 114 and second path 134 are collinear. Alternatively, the first light emission apparatus 108 and first light receiver apparatus 120 may be separately positioned in a separate apparatus such as at the one or more stations 174 of FIG. 4, whereby the first transmission signal 144 of FIG. 1 may be separately attained.

Figure 6:
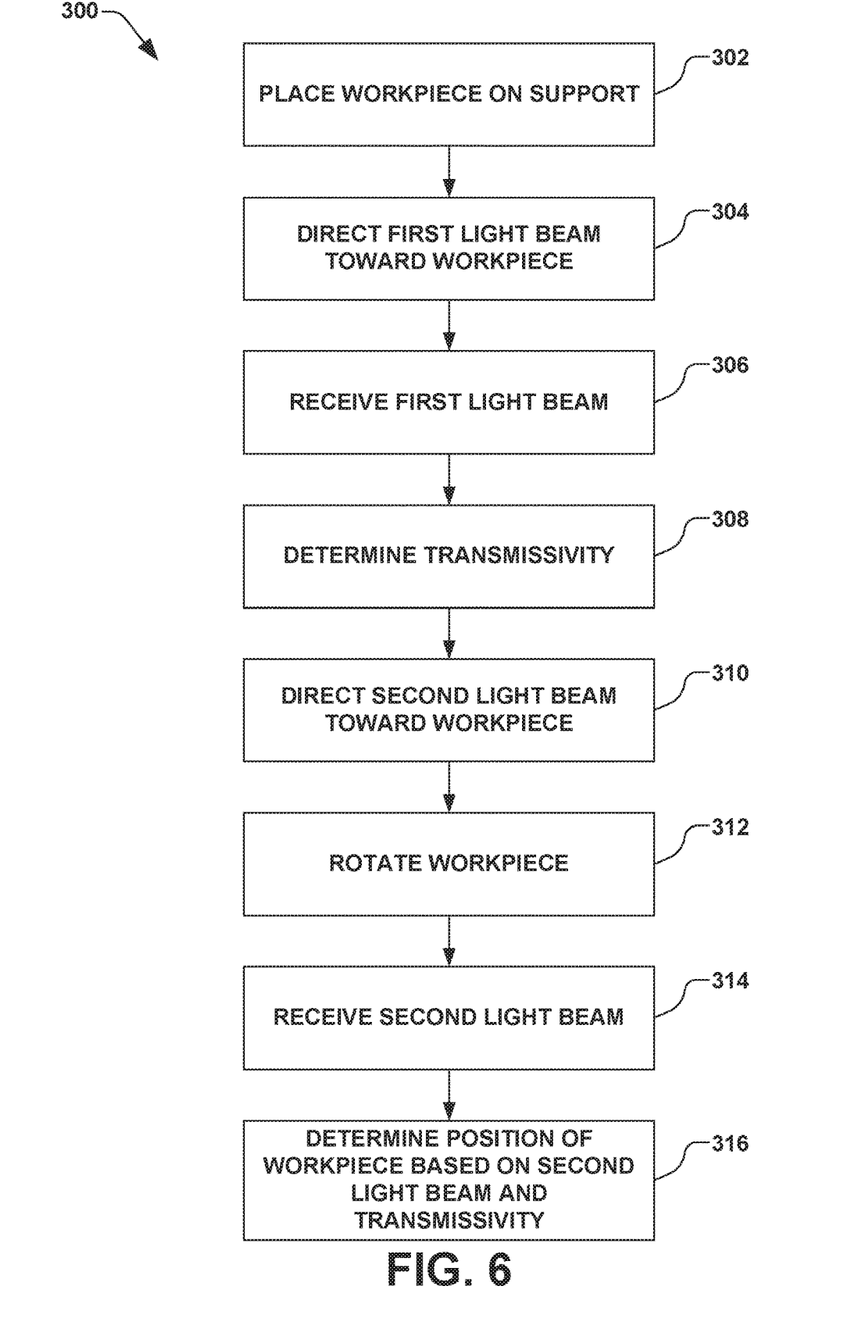
FIG. 6 is a block diagram illustrating an exemplary method for aligning workpieces according to another exemplary aspect of the disclosure.

In accordance with another exemplary aspect, a method 200 is provided for aligning a workpiece in FIG. 6. It should be noted that while exemplary methods are illustrated and described herein as a series of acts or events, it will be appreciated that the present disclosure is not limited by the illustrated ordering of such acts or events, as some steps may occur in different orders and/or concurrently with other steps apart from that shown and described herein, in accordance with the disclosure. In addition, not all illustrated steps may be required to implement a methodology in accordance with the present disclosure. Moreover, it will be appreciated that the methods may be implemented in association with the systems illustrated and described herein as well as in association with other systems not illustrated.

As illustrated in FIG. 6, the method 300 begins at act 302, wherein a workpiece is placed on a workpiece support. In act 304, a first beam of light is directed toward a first side of the workpiece along a first path. In one example, an entirety of the first beam of light is physically intercepted by the workpiece. Any portion of the first beam of light that is transmitted through the workpiece to a second side of the workpiece is received in act 306, wherein a transmissivity of the workpiece based on the first beam of light that is transmitted through the workpiece is determined in act 308.

A second beam of light is further directed toward a periphery of the workpiece along a second path in act 310, and the workpiece is rotated about a support axis in act 312. The first beam of light and second beam of light, for example, have equivalent wavelengths. The second beam of light is further received concurrent with the rotation of the workpiece in act 314, whereby a position of the workpiece with respect to the support axis is determined in act 316. The determination of the position of the workpiece in act 316 is based, at least in part, on a rotational position of the workpiece about the support axis and the second beam of light that is received, wherein the second beam of light is proportioned according to the determined transmissivity of the workpiece. The second beam of light, for example, is at least partially obscured by the periphery of the workpiece concurrent with the rotation of the workpiece.

Directing the first beam of light toward the first side of the workpiece in act 304, for example, comprises directing the first beam of light toward a central region of the workpiece. In another example, determining the position of the workpiece with respect to the support axis in act 316 comprises determining one or more of a rotational position of the workpiece about the support axis and a two-dimensional offset of a center of the workpiece from the support axis.

Although the disclosure has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the disclosure. In addition, while a particular feature of the disclosure may have been disclosed with respect to only one of several embodiments, such feature may be combined with one or more other features of the other embodiments as may be desired and advantageous for any given or particular application.

What is claimed is:

1. A workpiece alignment system, comprising:
    a first light emission apparatus configured to direct a first beam of light along a first path toward a first side of a workpiece plane associated with a workpiece;
    a first light receiver apparatus positioned along the first path and configured to receive the first beam of light on a second side of the workpiece plane, wherein the second side is opposite the first side;
    a workpiece support configured to selectively support the workpiece along the workpiece plane;
    a rotation device operably coupled to the workpiece support and configured to selectively rotate the workpiece support about a support axis;
    a second light emission apparatus positioned on one of the first side and second side of the workpiece plane and configured to direct a second beam of light along a second path, wherein the second path is associated with a peripheral region of the workpiece;
    a second light receiver apparatus configured to receive the second beam of light concurrent with the rotation of the workpiece support; and
    a controller configured to determine a transmissivity of the workpiece based on a total initial emittance of the first beam of light from the first light emission apparatus and a transmitted amount of the first beam of light that is received through the workpiece by the first light receiver apparatus when the workpiece fully intersects the first path, and wherein the controller is further configured to determine a position of the workpiece with respect to the support axis when the workpiece is supported and rotated via the workpiece support, wherein the determination of the position of the workpiece is based, at least in part, on a rotational position of the workpiece support, at least a portion of the second beam of light received by the second light receiver apparatus associated with the rotational position of the workpiece support, and the transmissivity of the workpiece.

2. The workpiece alignment system of claim 1, wherein the first path passes through a central region of the workpiece when the workpiece is supported on the workpiece support.

3. The workpiece alignment system of claim 1, wherein the first path passes through a central region of the workpiece when the workpiece is not supported on the workpiece support.

4. The workpiece alignment system of claim 1, wherein the first emission apparatus and second emission apparatus are configured to emit an equivalent wavelength of light.

5. The workpiece alignment system of claim 1, wherein the position of the workpiece comprises a two-dimensional offset of a center of the workpiece from the support axis along the workpiece plane.

6. The workpiece alignment system of claim 5, wherein the position of the workpiece further comprises a rotational position of the workpiece about the support axis.

7. The workpiece alignment system of claim 6, wherein the rotational position of the workpiece about the support axis is associated with an edge feature of the workpiece, and wherein the controller is further configured to determine the position of the workpiece with respect to the support axis based on the edge feature of the workpiece.

8. The workpiece alignment system of claim 1, wherein the controller is configured to determine a first waveform, wherein the first waveform is defined by the at least a portion of the second beam of light received by the second receiver at a plurality of rotational positions of the workpiece support, and wherein the controller is further configured to determine the position of the workpiece with respect to the support axis based on the first waveform.

9. The workpiece alignment system of claim 8, wherein the controller is further configured to proportion the first waveform based on the transmissivity of the workpiece.

10. The workpiece alignment system of claim 8, wherein the controller is configured to scale the at least a portion of the second beam of light received by the second receiver at the plurality of rotational positions of the workpiece support based on the transmissivity of the workpiece.

11. The workpiece alignment system of claim 1, wherein the transmitted amount of the first beam of light is defined as a percentage of a total initial emittance of the first beam of light.

12. The workpiece alignment system of claim 1, wherein the first path is associated with a central region of the workpiece, and wherein the central region of the workpiece intercepts an entirety of the first beam of light directed toward a surface of the workpiece.

13. The workpiece alignment system of claim 1, wherein the first light emission apparatus is positioned such that the first path is physically obstructed in its entirety by the workpiece.

14. The workpiece alignment system of claim 1, wherein the support axis is perpendicular to the workpiece plane.

15. The workpiece alignment system of claim 1, wherein a single light emission apparatus comprises the first light emission apparatus and second light emission apparatus, and wherein a single light receiver apparatus comprises the first light receiver apparatus and second light receiver apparatus, wherein the first path and second path are collinear.

16. A method for aligning a workpiece, the method comprising:
placing a workpiece on a workpiece support;
directing a first beam of light toward a first side of the workpiece along a first path, wherein an entirety of the first beam of light is physically intercepted by the workpiece;
receiving the first beam of light that is transmitted through the workpiece to a second side of the workpiece;
determining a transmissivity of the workpiece based on the first beam of light that is transmitted through the workpiece;
directing a second beam of light toward a periphery of the workpiece along a second path;
rotating the workpiece about a support axis;
receiving the second beam of light concurrent with the rotation of the workpiece; and
determining a position of the workpiece with respect to the support axis based, at least in part, on a rotational position of the workpiece about the support axis and the second beam of light that is received, wherein the second beam of light is proportioned according to the determined transmissivity of the workpiece.

17. The method of claim 16, wherein the second beam of light is at least partially obscured by the periphery of the workpiece.

18. The method of claim 16, wherein directing the first beam of light toward the first side of the workpiece comprises directing the first beam of light toward a central region of the workpiece.

19. The method of claim 16, wherein determining the position of the workpiece with respect to the support axis comprises determining one or more of a rotational position of the workpiece about the support axis and a two-dimensional offset of a center of the workpiece from the support axis.

20. The method of claim 16, wherein the first beam of light and second beam of light have equivalent wavelengths.

* * * * *